United States Patent [19]

Shapiro

[11] Patent Number: 4,767,445
[45] Date of Patent: Aug. 30, 1988

[54] HERBICIDAL ORTHO-(AZINYL)-BENZENESULFONAMIDES

[75] Inventor: Rafael Shapiro, Wilmington, Del.

[73] Assignee: E. I. Du Pont de Nemours and Company, Wilmington, Del.

[21] Appl. No.: 60,211

[22] Filed: Jun. 10, 1987

Related U.S. Application Data

[62] Division of Ser. No. 858,760, May 2, 1986, Pat. No. 4,693,744, which is a division of Ser. No. 667,600, Dec. 3, 1984, Pat. No. 4,606,754, which is a division of Ser. No. 437,325, Oct. 28, 1982, Pat. No. 4,494,980.

[51] Int. Cl.$^4$ ............... C07D 251/52; C07D 401/12; C07D 403/12; A01N 43/66

[52] U.S. Cl. ............................. 71/93; 544/182; 544/212; 544/207; 544/209

[58] Field of Search ................ 71/93; 544/182, 212, 544/207, 209

[56] References Cited

U.S. PATENT DOCUMENTS 4,606,755  8/1986  Rorer .................................. 544/212

Primary Examiner—John M. Ford

[57] ABSTRACT

This invention relates to novel ortho-(azinyl)benzenesulfonamides, such as N-[(4-methoxy-6-methylpyrimidin-2-yl)aminocarbonyl]-2-(2-pyridinyl)benzenesulfonamide, and their use as pre-emergent or post-emergent herbicides or plant growth regulants.

14 Claims, No Drawings

HERBICIDAL ORTHO-(AZINYL)-BENZENESULFONAMIDES

RELATED APPLICATIONS

This application is a divisional of copending application U.S. Ser. No. 858,760, filed May 2, 1986 now U.S. Pat. No. 4,693,744, which is a divisional of U.S. Ser. No. 667,600, filed Dec. 3, 1984, now U.S. Pat. No. 4,606,754, which is a divisional of U.S. Ser. No. 437,325, filed Oct. 28, 1982, now U.S. Pat. No. 4,494,980.

BACKGROUND OF THE INVENTION

The present invention relates to ortho-heterocyclic benzenesulfonylureas and, more particularly, to ortho-(mono, di or triazinyl)benzenesulfonylureas and to their use as pre- or post-emergent herbicides or as plant growth regulants.

U.S. patent application Ser. No. 337,932, filed Jan. 7, 1982, discloses and claimed orthoheterocyclic benzenesulfonylureas which are useful as herbicides or plant growth regulants. Compounds taught therein have the following general structure wherein Q can be, among other values, W can be O, S or NR;
the R substituents can be, with a few exceptions, H, lower alkyl or lower alkoxy;
X and Y can be $CH_3$ or $OCH_3$; and
Z can be CH or N.

U.S. patent application Ser. No. 337,934, filed Jan. 7, 1982, relates to ortho-heterocyclicbenzenesulfonamides, such as Z can be CH or N which are useful as general and selective herbicides and as plant growth regulants.

U.S. patent application Ser. No. 337,933, filed Jan. 7, 1982, also relates to ortho-heterocyclicbenzenesulfonylureas, in particular, ortho-furanylbenzenesulfonylureas, ortho-thienylbenzenesulfonylureas and ortho-pyrrolylbenzenesulfonylureas, and to their use as herbicides and plant growth regulants.

SUMMARY OF THE INVENTION

The present invention relates to compounds of Formula I, to suitable agricultural compositions containing them as an active ingredient and to their use as pre-emergent or post-emergent herbicides or plant growth regulants.

wherein
Q is $R_1$ is H, F, Cl, $CH_3$ or $OCH_3$;
$R_2$, $R_3$, $R_5$, $R_9$, $R_{10}$, $R_{11}$, $R_{12}$ and $R_{17}$ are independently H or $CH_3$;
$R_7$, $R_8$, $R_4$ and $R_6$ are independently H, $CH_3$ or $OCH_3$;
$R_{13}$, $R_{14}$, $R_{15}$ and $R_{16}$ are independently $CH_3$ or $OCH_3$;
X is $CH_3$, $OCH_3$ or Cl;
Y is $CH_3$, $C_2H_5$, $CH_2OCH_3$, $OCH_3$, $OC_2H_5$, $CH(OCH_3)_2$ $NH_2$, $NHCH_3$ or $N(CH_3)_2$;
Z is CH or N, provided that when X is Cl, then Z is CH and Y is $OCH_3$, $OC_2H_5$, $NHCH_3$ or $N(CH_3)_2$ and when $R_1$ is $CH_3$, it is in the 3-, 4- or 5-position of the benzene ring;
and their agriculturally suitable salts.

Preferred for reasons of their higher herbicidal activity and/or more favorable ease of synthesis are:
(1) Compounds of Formula I where $R_1$ and $R_{17}$ are H.
(2) Compounds of Preferred (1) where Y is $CH_3$, $OCH_3$, $CH_2OCH_3$ or $N(CH_3)_2$.
(3) Compounds of Preferred (2) where Q is (4) Compounds of Preferred (2) where Q is (5) Compounds of Preferred (2) where Q is (6) Compounds of Preferred (2) where Q is (7) Compounds of Preferred (2) where Q is (8) Compounds of preferred (2) where Q is Specifically preferred for reasons of their highest herbicidal activity and/or most favorable ease or synthesis are:

N-[(4-methoxy-6-methylpyrimidin-2-yl)aminocarbonyl]-2-(2-pyridinyl)benzenesulfonamide;

N-[(4,6-dimethylpyrimidin-2-yl)aminocarbonyl]-2-(2-pyridinyl)benzenesulfonamide;

N-[(4,6-dimethoxypyrimidin-2-yl)aminocarbonyl]-2-(2-pyridinyl)benzenesulfonamide; and N-[(4-methoxy-6-methylpyrimidin-2-yl)aminocarbonyl]-2-(2-pyrimidinyl)benzenesulfonamide.

DETAILED DESCRIPTION OF THE INVENTION

Synthesis

The ortho-heterocyclicbenzenesulfonylureas of Formula I can be prepared by reacting the appropriately substituted benzenesulfonamide with an appropriate methyl pyrimidinyl carbamate or methyl triazinyl carbamate in the presence of an equimolar amount of trimethylaluminum according to the procedure of Equation 1. Unless indicated otherwise, all temperatures are in °C.

Equation 1 wherein $R_1$, $R_{17}$, Q, X, Y, and Z are as previously defined.

The reaction of Equation 1 is best carried out in methylene chloride at 25° to 40° C. for 24 to 96 hours under a nitrogen atmosphere. The product can be isolated by the addition of an aqueous acetic acid solution followed by extraction of the product into methylene chloride or direct filtration of a product of low solubility. The product can ordinarily be purified by trituration with solvents such as n-butyl chloride or ether or by column chromatography.

Further details of this reaction and the preparation of the carbamates of Formula III can be found in U.S. Ser. No. 337,934.

Sulfonamides of Formula II may be prepared by the sequence of reactions outlined in Equation 2.

Equation 2 wherein $R_1$ and Q are as previously defined.

The compounds of Formula V are prepared by analogy with the teaching of J. G. Lombardino in *J. Org. Chem.*, 36, 1843.

An N-t-butyl sulfonamide of Formula IV is dissolved in an ethereal solvent, such as tetrahydrofuran, and two equivalents of n-butyllithium in hexane are added at 0°–25°. After 1–5 hours at 0°–25°, the compound of Formula V is formed. This is not isolated, but one equivalent of a copper (I) salt is added at −20° to 0°, followed by 1–1.5 equivalents of an appropriately substituted heteroaromatic iodide (VI). The reaction mixture is then heated at 40°–70° for 1–3 days, concentrated, poured onto aqueous ammonia, and filtered to provide the compound of Formula VII. The reaction of Formula 2c is conducted by heating a compound of Formula VII with 2–10 equivalents of trifluoroacetic acid or aqueous HBr with or without an inert solvent at 30°–70° for 1–3 days. The product II may be isolated as a trifluoroacetate or hydrobromide salt by evaporation of solvent and excess acid and trituration with ether. The free base may be obtained by neutralization of the salt with aqueous base, extraction into an organic solvent, and concentration of the organic extracts.

The compounds of Formula VI may be prepared according to methods known in the art, such as those reviewed in "The Chemistry of Heterocyclic Compounds," a series published by Interscience Publ., New York and London, the teachings of which are incorporated herein by reference. The iodopyridines are described in Vol. 14 of the above series, pp. 407–488. Iodopyrimidines are described by D. J. Brown and S. F. Mason in Vol. 16 of the above series. The preparation of iodopyrazines is taught by A. Hirschberg and P. E. Spoerri, *J. Org. Chem.*, 26, 1907 (1981) and iodopyridazines are described by D. L. Aldons and R. N. Castle in Vol. 28 of the Interscience series, pp. 240–241. The iodo-1,3,5-triazines are described by E. M. Smolin and L. Rapoport, in Vol. 13 of the above series, and a method for preparing iodo-1,2,4-triazines is taught by A. Rykowski and H. C. van der Plas, in *J. Org. Chem.*, 45, 881 (1980).

The present invention is further illustrated, in part, by the following examples.

EXAMPLE 1

N-(1,1-dimethylethyl)-2-(2-pyridinyl)benzenesulfonamide

To a solution of 30 g of N-(1,1-dimethylethyl)-2-(2-pyridinyl)benzenesulfonamide in 600 ml of tetrahydrofuran was added 190 ml of 1.6M butyllithium in hexane at −10° to 10°. The reaction mixture was allowed to stir at 25° for 1 hour, then cooled to −10° and 28 g of cuprous iodide was added. After 15 minutes stirring at 0°, 35 g of 2-iodopyridine was added and the mixture was heated to reflux for 16 hours. After cooling to 25°, 25 ml of acetic acid was added and solvent was removed in vacuo. A cold solution of aqueous ammonia was added and the precipitate was filtered. The solid was digested with methylene chloride and filtered. The filtrate was concentrated, triturated with n-chlorobutane, and the solid was filtered to afford 36 g (78%) of product, m.p. 147°–150°. NMR(CDCl$_3$)δ: 1.3 (s, 9), 7.1–8.7 (m, 9).

EXAMPLE 2

2-(2-pyridinyl)benzenesulfonamide

A solution of 14.8 g of the sulfonamide from Example 1 and 10 ml of 48% hydrobromic acid in 100 ml of methanol was heated at 40°–45° for 16 hours, concentrated, and neutralized with aqueous sodium bicarbonate. The solid was filtered, washed with ice-water, and air-dried to afford 6.0 g of product, m.p. 186°–190°. NMR(CDCl$_3$/DMSO-d$_6$)δ: 7.5 (m, 7), 8.1 (m, 2), 8.6 (d, 1). IR(Nujol) 3300, 3260 cm$^{-1}$. m/e M+234.

EXAMPLE 3

N-[(4,6-dimethoxypyrimidin-2-yl)aminocarbonyl]-2-(2-pyridinyl)benzenesulfonamide A solution of 1.2 g of the compound from Example 2 and 1.3 g of methyl N-(4,6-dimethoxypyrimidin-2-yl)carbamate in 50 ml of methylene chloride was stirred under nitrogen and 3.4 ml of a 2N solution of trimethylaluminum in toluene was added. After heating at reflux for 4 days, the solution was cooled to 0°, 3 ml of 2N HCl (aq.) was added, the mixture was partitioned between methylene chloride and water. The organic layer was concentrated and the residue was chromatographed on silica gel to afford 0.9 g of the product, m.p. 175°–176°. NMR (DMSO-d$_6$)δ: 3.8 (s, 6), 6.0 (s, 1), 7.2–8.3 (m). m/e (M$^+$+1) 416. IR 1700 cm$^{-1}$.

Using the procedures described in the equations and Examples 1–3 above, the compounds described in the following Tables I–X can be prepared.

TABLE I

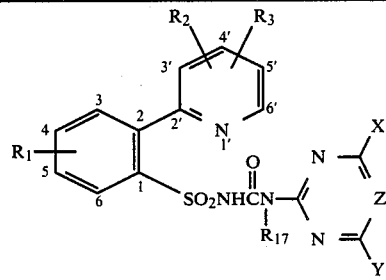

| R$_1$ | R$_2$ | R$_3$ | R$_{17}$ | X | Y | Z | m.p. (°C.) |
|---|---|---|---|---|---|---|---|
| H | H | H | H | CH$_3$ | CH$_3$ | CH | 171–174° |
| H | H | H | H | CH$_3$ | OCH$_3$ | CH | 180–184° |
| H | H | H | H | OCH$_3$ | OCH$_3$ | CH | 175–176° |
| H | H | H | H | CH$_3$ | CH$_3$ | N | |
| H | H | H | H | CH$_3$ | OCH$_3$ | N | 160–173° |
| H | H | H | H | OCH$_3$ | OCH$_3$ | N | 172–205° |
| H | H | H | H | CH$_3$ | CH$_2$OCH$_3$ | CH | |
| H | H | H | H | CH$_3$ | CH(OCH$_3$)$_2$ | CH | |
| H | H | H | H | OCH$_3$ | N(CH$_3$)$_2$ | N | |

TABLE I-continued

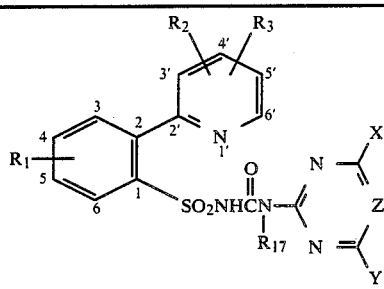

| R₁ | R₂ | R₃ | R₁₇ | X | Y | Z | m.p. (°C.) |
|---|---|---|---|---|---|---|---|
| H | H | H | H | OCH₃ | NH₂ | CH | |
| H | H | H | H | Cl | OCH₃ | CH | |
| H | H | H | H | OCH₃ | NHCH₃ | CH | |
| H | H | H | H | CH₃ | CH₂OCH₃ | N | |
| H | H | H | H | Cl | CH₃ | CH | |
| H | H | H | H | OCH₃ | CH(OCH₃)₂ | N | |
| H | 4'-CH₃ | H | H | CH₃ | CH₃ | CH | |
| H | 4'-CH₃ | 6'-CH₃ | H | CH₃ | OCH₃ | CH | |
| H | 5'-CH₃ | H | H | OCH₃ | OCH₃ | N | |
| H | 3'-CH₃ | H | H | OCH₃ | OCH₃ | CH | |
| H | 3'-CH₃ | 5'-CH₃ | H | CH₃ | OCH₃ | CH | |
| H | 6'-CH₃ | H | H | OCH₃ | CH₃ | N | |
| H | H | H | CH₃ | CH₃ | CH₃ | CH | |
| H | H | H | CH₃ | OCH₃ | OCH₃ | CH | |
| H | 6'-CH₃ | H | H | CH₃ | CH₃ | N | |
| H | 4'-CH₃ | H | H | OCH₃ | CH₂OCH₃ | N | |
| H | 5'-CH₃ | H | H | CH₃ | CH₃ | CH | |
| H | H | H | H | OCH₃ | CH(OCH₃)₂ | CH | |
| 3-F | H | H | H | CH₃ | CH₃ | N | |
| 3-F | H | H | H | OCH₃ | CH₃ | N | |
| 3-F | H | H | H | CH₃ | N(CH₃)₂ | CH | |
| 3-F | H | H | H | Cl | OCH₃ | CH | |
| 3-F | H | H | CH₃ | OCH₃ | NH₂ | N | |
| 3-F | H | H | H | CH₃ | OCH₃ | N | |
| 4-Cl | H | H | H | OCH₃ | CH₃ | CH | |
| 4-Cl | H | H | H | CH₃ | OC₂H₅ | CH | |
| 4-Cl | H | H | H | OCH₃ | C₂H₅ | N | |
| 4-Cl | 6'-CH₃ | H | H | Cl | CH₂OCH₃ | N | |
| 4-Cl | H | H | H | OCH₃ | OCH₃ | CH | |
| 4-Cl | H | H | CH₃ | CH₃ | OCH₃ | CH | |
| 5-CH₃ | H | H | H | OCH₃ | NHCH₃ | N | |
| 5-CH₃ | H | H | H | CH₃ | C₂H₅ | N | |
| 5-CH₃ | H | H | H | OCH₃ | CH₃ | CH | |
| 5-CH₃ | H | H | H | CH₃ | CH₃ | CH | |
| 5-CH₃ | H | H | H | OCH₃ | CH₃ | N | |
| 4-OCH₃ | H | H | H | CH₃ | OCH₃ | N | |
| 4-OCH₃ | H | H | H | OCH₃ | OCH₃ | CH | |
| 4-OCH₃ | H | H | H | CH₃ | CH₃ | CH | |
| 4-OCH₃ | H | H | H | OCH₃ | OCH₃ | N | |

TABLE II

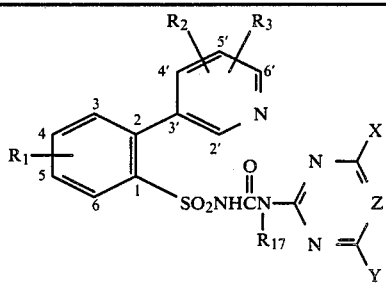

| R₁ | R₂ | R₃ | R₁₇ | X | Y | Z | m.p. (°C.) |
|---|---|---|---|---|---|---|---|
| H | H | H | H | CH₃ | CH₃ | CH | |
| H | H | H | H | CH₃ | OCH₃ | CH | |
| H | H | H | H | OCH₃ | OCH₃ | CH | |
| H | H | H | H | CH₃ | CH₃ | N | |
| H | H | H | H | CH₃ | OCH₃ | N | |
| H | H | H | H | OCH₃ | OCH₃ | N | |
| H | H | H | H | CH₃ | CH₂OCH₃ | CH | |
| H | H | H | H | CH₃ | CH(OCH₃)₂ | CH | |

TABLE II-continued

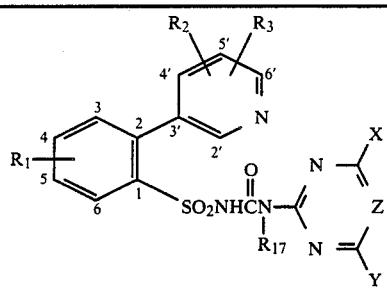

| R₁ | R₂ | R₃ | R₁₇ | X | Y | Z | m.p. (°C.) |
|---|---|---|---|---|---|---|---|
| H | H | H | H | OCH₃ | N(CH₃)₂ | N | |
| H | H | H | H | OCH₃ | NH₂ | CH | |
| H | H | H | H | Cl | OCH₃ | CH | |
| H | H | H | H | OCH₃ | NHCH₃ | CH | |
| H | H | H | H | CH₃ | CH₂OCH₃ | N | |
| H | H | H | H | Cl | CH₃ | CH | |
| H | H | H | H | OCH₃ | CH(OCH₃)₂ | N | |
| H | 2'-CH₃ | H | H | OCH₃ | CH₃ | CH | |
| H | 5'-CH₃ | 6'-CH₃ | H | OCH₃ | CH₃ | N | |
| H | 6'-CH₃ | H | H | CH₃ | CH₃ | CH | |
| H | 5'-CH₃ | H | H | CH₃ | OCH₃ | CH | |
| H | 4'-CH₃ | 6'-CH₃ | H | OCH₃ | OCH₃ | CH | |
| H | 2'-CH₃ | H | H | OCH₃ | OCH₃ | N | |
| H | H | H | CH₃ | CH₃ | CH₃ | CH | |
| H | H | H | CH₃ | OCH₃ | OCH₃ | CH | |
| H | 6'-CH₃ | H | H | CH₃ | CH₃ | N | |
| H | H | H | H | OCH₃ | CH₂OCH₃ | N | |
| H | 4'-CH₃ | H | H | CH₃ | CH₃ | CH | |
| H | H | H | H | OCH₃ | CH(OCH₃)₂ | CH | |
| 6-F | H | H | H | CH₃ | CH₃ | N | |
| 6-F | H | H | H | OCH₃ | CH₃ | N | |
| 6-F | H | H | H | CH₃ | N(CH₃)₂ | CH | |
| 6-F | H | H | H | Cl | OCH₃ | CH | |
| 6-F | H | H | CH₃ | OCH₃ | NH₂ | N | |
| 6-F | H | H | H | CH₃ | OCH₃ | N | |
| 3-Cl | H | H | H | OCH₃ | CH₃ | CH | |
| 3-Cl | H | H | H | CH₃ | OC₂H₅ | CH | |
| 3-Cl | H | H | H | OCH₃ | C₂H₅ | N | |
| 3-Cl | H | H | H | Cl | CH₂OCH₃ | N | |
| 3-Cl | H | H | H | OCH₃ | OCH₃ | CH | |
| 3-Cl | H | H | CH₃ | CH₃ | OCH₃ | CH | |
| 4-CH₃ | H | H | H | OCH₃ | NHCH₃ | N | |
| 4-CH₃ | 5'-CH₃ | H | H | CH₃ | C₂H₅ | N | |
| 4-CH₃ | H | H | H | OCH₃ | CH₃ | CH | |
| 4-CH₃ | H | H | H | CH₃ | CH₃ | CH | |
| 4-CH₃ | H | H | H | OCH₃ | CH₃ | N | |
| 5-OCH₃ | H | H | H | CH₃ | OCH₃ | N | |
| 5-OCH₃ | H | H | H | OCH₃ | OCH₃ | CH | |
| 5-OCH₃ | H | H | H | CH₃ | CH₃ | CH | |
| 5-OCH₃ | H | H | H | OCH₃ | OCH₃ | N | |

TABLE III

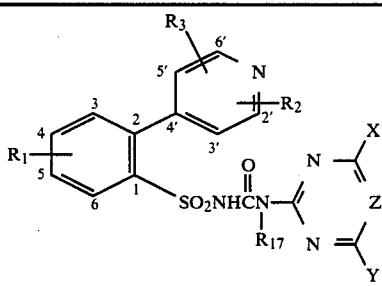

| R₁ | R₂ | R₃ | R₁₇ | X | Y | Z | m.p. (°C.) |
|---|---|---|---|---|---|---|---|
| H | H | H | H | CH₃ | CH₃ | CH | |
| H | H | H | H | CH₃ | OCH₃ | CH | |
| H | H | H | H | OCH₃ | OCH₃ | CH | |
| H | H | H | H | CH₃ | CH₃ | N | |
| H | H | H | H | CH₃ | OCH₃ | N | |
| H | H | H | H | OCH₃ | OCH₃ | N | |
| H | H | H | H | CH₃ | CH₂OCH₃ | CH | |

TABLE III-continued

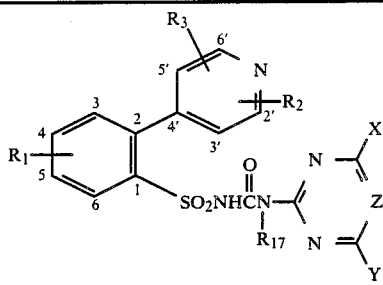

| R₁ | R₂ | R₃ | R₁₇ | X | Y | Z | m.p. (°C.) |
|---|---|---|---|---|---|---|---|
| H | H | H | H | CH₃ | CH(OCH₃)₂ | CH | |
| H | H | H | H | OCH₃ | N(CH₃)₂ | N | |
| H | H | H | H | OCH₃ | NH₂ | CH | |
| H | H | H | H | Cl | OCH₃ | CH | |
| H | H | H | H | OCH₃ | NHCH₃ | CH | |
| H | H | H | H | CH₃ | CH₂OCH₃ | N | |
| H | H | H | H | Cl | CH₃ | CH | |
| H | H | H | H | OCH₃ | CH(OCH₃)₂ | N | |
| H | 2'-CH₃ | H | H | CH₃ | OCH₃ | N | |
| H | 2'-CH₃ | 6'-CH₃ | H | CH₃ | OCH₃ | CH | |
| H | 3'-CH₃ | H | H | CH₃ | CH₃ | CH | |
| H | 2'-CH₃ | H | H | OCH₃ | OCH₃ | N | |
| H | 3'-CH₃ | 6'-CH₃ | H | OCH₃ | OCH₃ | CH | |
| H | 2'-CH₃ | H | H | CH₃ | OCH₃ | CH | |
| H | H | H | CH₃ | CH₃ | CH₃ | CH | |
| H | H | H | CH₃ | OCH₃ | OCH₃ | CH | |
| H | 2'-CH₃ | H | H | CH₃ | CH₃ | N | |
| H | H | H | H | OCH₃ | CH₂OCH₃ | N | |
| H | 3'-CH₃ | H | H | CH₃ | CH₃ | CH | |
| H | H | H | H | OCH₃ | CH(OCH₃)₂ | CH | |
| 5-F | H | H | H | CH₃ | CH₃ | N | |
| 5-F | H | H | H | OCH₃ | CH₃ | N | |
| 5-F | H | H | H | CH₃ | N(CH₃)₂ | CH | |
| 5-F | H | H | H | Cl | OCH₃ | CH | |
| 5-F | H | H | CH₃ | OCH₃ | NH₂ | N | |
| 5-F | H | H | H | CH₃ | OCH₃ | N | |
| 4-Cl | H | H | H | OCH₃ | CH₃ | CH | |
| 4-Cl | H | H | H | CH₃ | OC₂H₅ | CH | |
| 4-Cl | H | H | H | OCH₃ | C₂H₅ | N | |
| 4-Cl | H | H | H | Cl | CH₂OCH₃ | N | |
| 4-Cl | H | H | H | OCH₃ | OCH₃ | CH | |
| 4-Cl | 2'-CH₃ | 6'-CH₃ | CH₃ | CH₃ | OCH₃ | CH | |
| 3-CH₃ | H | H | H | OCH₃ | NHCH₃ | N | |
| 3-CH₃ | H | H | H | CH₃ | C₂H₅ | N | |
| 3-CH₃ | H | H | H | OCH₃ | CH₃ | CH | |
| 3-CH₃ | H | H | H | CH₃ | CH₃ | CH | |
| 3-CH₃ | H | H | H | OCH₃ | CH₃ | N | |
| 3-OCH₃ | H | H | H | CH₃ | OCH₃ | N | |
| 3-OCH₃ | H | H | H | OCH₃ | OCH₃ | CH | |
| 3-OCH₃ | H | H | H | CH₃ | CH₃ | CH | |
| 3-OCH₃ | H | H | H | OCH₃ | OCH₃ | N | |

TABLE IV

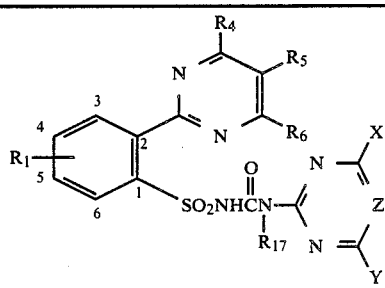

| R₁ | R₄ | R₅ | R₆ | R₁₇ | X | Y | Z | m.p. (°C.) |
|---|---|---|---|---|---|---|---|---|
| H | H | H | H | H | CH₃ | CH₃ | CH | |
| H | H | H | H | H | CH₃ | OCH₃ | CH | 178–185° |
| H | H | H | H | H | OCH₃ | OCH₃ | CH | 197–210° |
| H | H | H | H | H | CH₃ | CH₃ | N | |
| H | H | H | H | H | CH₃ | OCH₃ | N | |
| H | H | H | H | H | OCH₃ | OCH₃ | N | |
| H | H | H | H | H | CH₃ | CH₂OCH₃ | CH | |

TABLE IV-continued

| $R_1$ | $R_4$ | $R_5$ | $R_6$ | $R_{17}$ | X | Y | Z | m.p. (°C.) |
|---|---|---|---|---|---|---|---|---|
| H | H | H | H | H | $CH_3$ | $CH(OCH_3)_2$ | CH | |
| H | H | H | H | H | $CH_3$ | $N(CH_3)_2$ | CH | |
| H | H | H | H | H | $OCH_3$ | $NH_2$ | CH | |
| H | H | H | H | H | $OCH_3$ | $NHCH_3$ | CH | |
| H | H | H | H | H | $OCH_3$ | $CH(OCH_3)_2$ | CH | |
| H | H | H | H | H | Cl | $OCH_3$ | CH | |
| H | H | H | H | H | $CH_3$ | $CH_2OCH_3$ | N | |
| H | H | H | H | H | $OCH_3$ | $N(CH_3)_2$ | N | |
| H | H | H | H | H | $CH_3$ | $CH(OCH_3)_2$ | N | |
| H | H | H | H | H | $OCH_3$ | $CH_2OCH_3$ | N | |
| H | $CH_3$ | H | H | H | $CH_3$ | $OCH_3$ | N | |
| H | $CH_3$ | H | $CH_3$ | H | $OCH_3$ | $OCH_3$ | N | |
| H | $OCH_3$ | H | $CH_3$ | H | $CH_3$ | $CH(OCH_3)_2$ | N | |
| H | $OCH_3$ | H | H | H | $CH_3$ | $CH(OCH_3)_2$ | N | |
| 3-Cl | H | H | H | H | $CH_3$ | $OCH_3$ | CH | |
| 4-Cl | H | H | H | H | $OCH_3$ | $OCH_3$ | N | |
| 4-Cl | H | H | H | H | $CH_3$ | $OCH_3$ | N | |
| 4-Cl | $CH_3$ | H | $CH_3$ | H | $CH_3$ | $CH_3$ | CH | |
| 4-Cl | $OCH_3$ | H | $OCH_3$ | H | $OCH_3$ | $OCH_3$ | CH | |
| 4-Cl | H | H | H | H | $OCH_3$ | $OCH_3$ | N | |
| 4-Cl | H | $CH_3$ | H | H | $OCH_3$ | $OCH_3$ | CH | |
| 5-Cl | H | H | H | $CH_3$ | $CH_3$ | $OCH_3$ | CH | |
| 3-$CH_3$ | H | H | H | H | $CH_3$ | $CH_3$ | CH | |
| 5-$CH_3$ | H | H | H | H | $OCH_3$ | $CH_2OCH_3$ | N | |
| 4-$CH_3$ | H | H | H | H | $CH_3$ | $CH(OCH_3)_2$ | CH | |
| 4-$CH_3$ | H | H | H | H | $CH_3$ | $N(CH_3)_2$ | N | |
| 4-$CH_3$ | H | H | H | H | $OCH_3$ | $OCH_3$ | CH | |
| 4-$CH_3$ | $CH_3$ | $CH_3$ | $OCH_3$ | H | $OCH_3$ | $CH_3$ | CH | |
| 4-$OCH_3$ | H | H | H | $CH_3$ | $CH_3$ | $CH_3$ | N | |
| 3-$OCH_3$ | $CH_3$ | $CH_3$ | H | H | $OCH_3$ | $OCH_3$ | N | |
| 6-$OCH_3$ | H | H | H | H | $OCH_3$ | $OCH_3$ | N | |
| 6-$OCH_3$ | H | H | H | H | $CH_3$ | $OCH_3$ | CH | |
| 6-$OCH_3$ | H | H | H | H | $CH_3$ | $CH_3$ | CH | |
| 6-F | H | H | H | H | $OCH_3$ | $OCH_3$ | N | |
| 5-F | H | H | H | H | $CH_3$ | $OCH_3$ | N | |
| 3-F | H | H | H | H | $CH_3$ | $CH_2OCH_3$ | CH | |
| 3-F | H | H | H | H | $OCH_3$ | $CH(OCH_3)_2$ | CH | |
| 3-F | H | H | H | H | $CH_3$ | $N(CH_3)_2$ | N | |
| 3-F | H | H | H | $CH_3$ | $CH_3$ | $OCH_3$ | CH | |
| 3-F | $OCH_3$ | $CH_3$ | $OCH_3$ | H | $CH_3$ | $OCH_3$ | N | |

TABLE V

| $R_1$ | $R_7$ | $R_8$ | $R_{17}$ | X | Y | Z | m.p. (°C.) |
|---|---|---|---|---|---|---|---|
| H | H | H | H | $CH_3$ | $CH_3$ | CH | |
| H | H | H | H | $CH_3$ | $OCH_3$ | CH | |
| H | H | H | H | $OCH_3$ | $OCH_3$ | CH | |
| H | H | H | H | $CH_3$ | $CH_3$ | N | |
| H | H | H | H | $CH_3$ | $OCH_3$ | N | |
| H | H | H | H | $OCH_3$ | $OCH_3$ | N | |
| H | H | H | H | $CH_3$ | $CH_2OCH_3$ | CH | |
| H | H | H | H | $CH_3$ | $CH(OCH_3)_2$ | CH | |
| H | H | H | H | $OCH_3$ | $N(CH_3)_2$ | N | |

TABLE V-continued

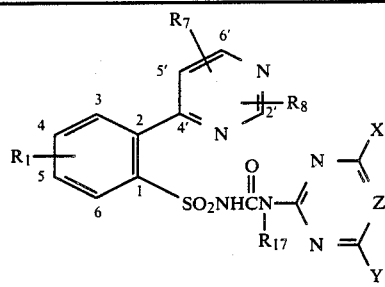

| R₁ | R₇ | R₈ | R₁₇ | X | Y | Z | m.p. (°C.) |
|---|---|---|---|---|---|---|---|
| H | H | H | H | OCH₃ | NH₂ | CH | |
| H | H | H | H | Cl | OCH₃ | CH | |
| H | H | H | H | OCH₃ | NHCH₃ | CH | |
| H | H | H | H | CH₃ | CH₂OCH₃ | N | |
| H | H | H | H | Cl | CH₃ | CH | |
| H | H | H | H | OCH₃ | CH(OCH₃)₂ | N | |
| H | 2'-CH₃ | H | H | CH₃ | CH₃ | CH | |
| H | 2'-CH₃ | 6'-OCH₃ | H | CH₃ | OCH₃ | N | |
| H | 2'-OCH₃ | H | H | OCH₃ | OCH₃ | N | |
| H | 5'-CH₃ | H | H | OCH₃ | OCH₃ | CH | |
| H | 2'-OCH₃ | 5'-CH₃ | H | CH₃ | CH₃ | CH | |
| H | 6'-CH₃ | H | H | OCH₃ | CH₃ | CH | |
| H | H | H | CH₃ | CH₃ | CH₃ | CH | |
| H | H | H | CH₃ | OCH₃ | OCH₃ | CH | |
| H | 2'-CH₃ | H | H | CH₃ | CH₃ | N | |
| H | H | H | H | OCH₃ | CH₂OCH₃ | N | |
| H | 6'-CH₃ | H | H | CH₃ | CH₃ | CH | |
| H | H | H | H | OCH₃ | CH(OCH₃)₂ | CH | |
| 4-F | H | H | H | CH₃ | CH₃ | N | |
| 4-F | H | H | H | OCH₃ | CH₃ | N | |
| 4-F | H | H | H | CH₃ | N(CH₃)₂ | CH | |
| 4-F | H | H | H | Cl | OCH₃ | CH | |
| 4-F | H | H | CH₃ | OCH₃ | NH₂ | N | |
| 4-F | H | H | H | CH₃ | OCH₃ | N | |
| 5-Cl | H | H | H | OCH₃ | CH₃ | CH | |
| 5-Cl | H | H | H | CH₃ | OC₂H₅ | CH | |
| 5-Cl | H | H | H | OCH₃ | C₂H₅ | N | |
| 5-Cl | H | H | H | Cl | CH₂OCH₃ | N | |
| 5-Cl | H | H | H | OCH₃ | OCH₃ | CH | |
| 5-Cl | H | H | CH₃ | CH₃ | OCH₃ | CH | |
| 3-CH₃ | H | H | H | OCH₃ | NHCH₃ | N | |
| 3-CH₃ | H | H | H | CH₃ | C₂H₅ | N | |
| 3-CH₃ | H | H | H | OCH₃ | CH₃ | CH | |
| 3-CH₃ | 2'-CH₃ | H | H | CH₃ | CH₃ | CH | |
| 3-CH₃ | H | H | H | OCH₃ | CH₃ | N | |
| 4-OCH₃ | H | H | H | OCH₃ | OCH₃ | N | |
| 4-OCH₃ | H | H | H | OCH₃ | OCH₃ | CH | |
| 4-OCH₃ | H | H | H | CH₃ | CH₃ | CH | |
| 4-OCH₃ | H | H | H | OCH₃ | OCH₃ | N | |

TABLE VI

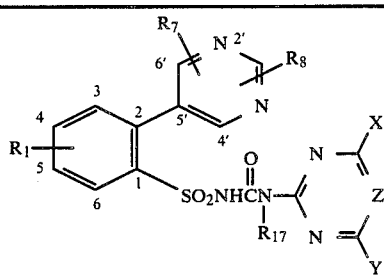

| R₁ | R₇ | R₈ | R₁₇ | X | Y | Z | m.p. (°C.) |
|---|---|---|---|---|---|---|---|
| H | H | H | H | CH₃ | CH₃ | CH | |
| H | H | H | H | CH₃ | OCH₃ | CH | |
| H | H | H | H | OCH₃ | OCH₃ | CH | |
| H | H | H | H | CH₃ | CH₃ | N | |
| H | H | H | H | CH₃ | OCH₃ | N | |
| H | H | H | H | OCH₃ | OCH₃ | N | |
| H | H | H | H | CH₃ | CH₂OCH₃ | CH | |
| H | H | H | H | CH₃ | CH(OCH₃)₂ | CH | |
| H | H | H | H | OCH₃ | N(CH₃)₂ | N | |
| H | H | H | H | OCH₃ | NH₂ | CH | |

TABLE VI-continued

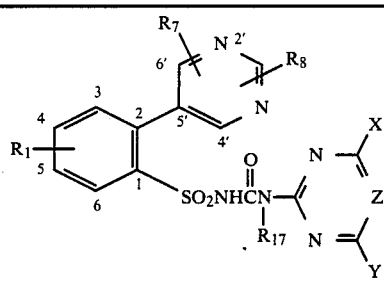

| R₁ | R₇ | R₈ | R₁₇ | X | Y | Z | m.p. (°C.) |
|---|---|---|---|---|---|---|---|
| H | H | H | H | Cl | OCH₃ | CH | |
| H | H | H | H | OCH₃ | NHCH₃ | CH | |
| H | H | H | H | CH₃ | CH₂OCH₃ | N | |
| H | H | H | H | Cl | CH₃ | CH | |
| H | H | H | H | OCH₃ | CH(OCH₃)₂ | N | |
| H | 2'-OCH₃ | H | H | CH₃ | CH₃ | CH | |
| H | 2'-CH₃ | 4'-CH₃ | H | CH₃ | OCH₃ | N | |
| H | 4'-OCH₃ | H | H | CH₃ | CH₃ | CH | |
| H | 2'-CH₃ | H | H | OCH₃ | OCH₃ | CH | |
| H | 4'-CH₃ | 6'-CH₃ | H | OCH₃ | OCH₃ | N | |
| H | 2'-CH₃ | H | H | OCH₃ | OCH₃ | N | |
| H | H | H | CH₃ | CH₃ | CH₃ | CH | |
| H | H | H | H | OCH₃ | OCH₃ | CH | |
| H | 2'-CH₃ | H | H | CH₃ | CH₃ | N | |
| H | H | H | H | OCH₃ | CH₂OCH₃ | N | |
| H | 4'-CH₃ | 6'-CH₃ | H | CH₃ | CH₃ | CH | |
| H | H | H | H | OCH₃ | CH(OCH₃)₂ | CH | |
| 5-F | H | H | H | CH₃ | CH₃ | N | |
| 5-F | H | H | H | OCH₃ | CH₃ | N | |
| 5-F | H | H | H | CH₃ | N(CH₃)₂ | CH | |
| 5-F | H | H | H | Cl | OCH₃ | CH | |
| 5-F | H | H | CH₃ | OCH₃ | NH₂ | N | |
| 5-F | H | H | H | CH₃ | OCH₃ | N | |
| 3-Cl | H | H | H | OCH₃ | CH₃ | CH | |
| 3-Cl | H | H | H | CH₃ | OC₂H₅ | CH | |
| 3-Cl | H | H | H | OCH₃ | C₂H₅ | N | |
| 3-Cl | H | H | H | Cl | CH₂OCH₃ | N | |
| 3-Cl | H | H | H | OCH₃ | OCH₃ | CH | |
| 3-Cl | H | H | CH₃ | CH₃ | OCH₃ | CH | |
| 4-CH₃ | H | H | H | OCH₃ | NHCH₃ | N | |
| 4-CH₃ | H | H | H | CH₃ | C₂H₅ | N | |
| 4-CH₃ | H | H | H | OCH₃ | CH₃ | CH | |
| 4-CH₃ | H | H | H | CH₃ | CH₃ | CH | |
| 4-CH₃ | 2'-CH₃ | H | H | OCH₃ | CH₃ | N | |
| 5-OCH₃ | H | H | H | CH₃ | OCH₃ | N | |
| 5-OCH₃ | H | H | H | OCH₃ | OCH₃ | CH | |
| 5-OCH₃ | H | H | H | CH₃ | CH₃ | CH | |
| 5-OCH₃ | H | H | H | OCH₃ | OCH₃ | N | |

TABLE VII

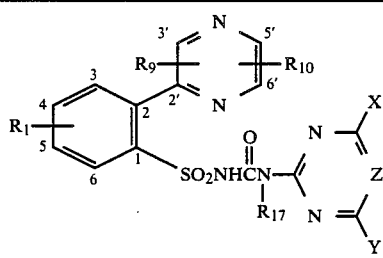

| R₁ | R₉ | R₁₀ | R₁₇ | X | Y | Z | m.p. (°C.) |
|---|---|---|---|---|---|---|---|
| H | H | H | H | CH₃ | CH₃ | CH | 212–217° d |
| H | H | H | H | CH₃ | OCH₃ | CH | 178° |
| H | H | H | H | OCH₃ | OCH₃ | CH | 178–179° |
| H | H | H | H | CH₃ | CH₃ | N | |
| H | H | H | H | OCH₃ | OCH₃ | N | |
| H | H | H | H | CH₃ | CH₂OCH₃ | CH | |
| H | H | H | H | CH₃ | CH(OCH₃)₂ | CH | |
| H | H | H | H | OCH₃ | N(CH₃)₂ | N | |
| H | H | H | H | OCH₃ | NH₂ | CH | |
| H | H | H | H | Cl | OCH₃ | CH | |

TABLE VII-continued

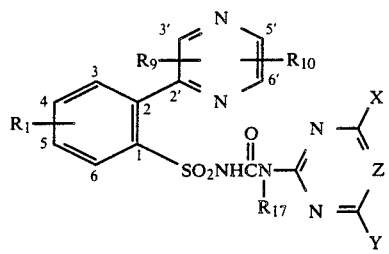

| R₁ | R₉ | R₁₀ | R₁₇ | X | Y | Z | m.p. (°C.) |
|---|---|---|---|---|---|---|---|
| H | H | H | H | OCH₃ | NHCH₃ | CH | |
| H | H | H | H | CH₃ | CH₂OCH₃ | N | |
| H | H | H | H | Cl | CH₃ | CH | |
| H | H | H | H | OCH₃ | CH(OCH₃)₂ | N | |
| H | 3'-CH₃ | H | H | CH₃ | OCH₃ | CH | |
| H | 5'-CH₃ | 6'-CH₃ | H | CH₃ | OCH₃ | CH | |
| H | 5'-CH₃ | H | H | CH₃ | CH₃ | CH | |
| H | 6'-CH₃ | H | H | OCH₃ | OCH₃ | N | |
| H | 3'-CH₃ | 6'-CH₃ | H | OCH₃ | CH₃ | N | |
| H | 3'-CH₃ | H | H | OCH₃ | OCH₃ | CH | |
| H | H | H | CH₃ | CH₃ | CH₃ | CH | |
| H | H | H | CH₃ | OCH₃ | OCH₃ | CH | |
| H | 6'-CH₃ | H | H | CH₃ | CH₃ | N | |
| H | H | H | H | OCH₃ | CH₂OCH₃ | N | |
| H | 5'-CH₃ | 6'-CH₃ | H | CH₃ | CH₃ | CH | |
| H | H | H | H | OCH₃ | CH(OCH₃)₂ | CH | |
| 3-F | H | H | H | CH₃ | CH₃ | N | |
| 3-F | H | H | H | OCH₃ | CH₃ | N | |
| 3-F | H | H | H | CH₃ | N(CH₃)₂ | CH | |
| 3-F | H | H | H | Cl | OCH₃ | CH | |
| 3-F | H | H | CH₃ | OCH₃ | NH₂ | N | |
| 3-F | H | H | H | CH₃ | OCH₃ | N | |
| 4-Cl | H | H | H | OCH₃ | CH₃ | CH | |
| 4-Cl | H | H | H | CH₃ | OC₂H₅ | CH | |
| 4-Cl | H | H | H | OCH₃ | C₂H₅ | N | |
| 4-Cl | H | H | H | Cl | CH₂OCH₃ | N | |
| 4-Cl | 6'-CH₃ | H | H | OCH₃ | OCH₃ | CH | |
| 4-Cl | H | H | CH₃ | CH₃ | OCH₃ | CH | |
| 5-CH₃ | H | H | H | OCH₃ | NHCH₃ | N | |
| 5-CH₃ | H | H | H | CH₃ | C₂H₅ | N | |
| 5-CH₃ | H | H | H | OCH₃ | CH₃ | CH | |
| 5-CH₃ | H | H | H | CH₃ | CH₃ | CH | |
| 5-CH₃ | H | H | H | OCH₃ | CH₃ | N | |
| 6-OCH₃ | H | H | H | CH₃ | OCH₃ | N | |
| 6-OCH₃ | H | H | H | OCH₃ | OCH₃ | CH | |
| 6-OCH₃ | H | H | H | CH₃ | CH₃ | CH | |
| 6-OCH₃ | H | H | H | OCH₃ | OCH₃ | N | |

TABLE VIII

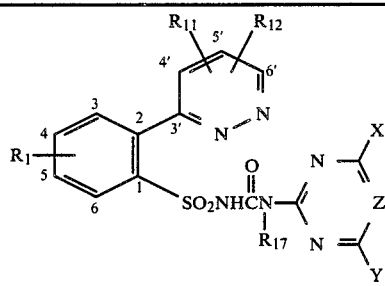

| R₁ | R₁₁ | R₁₂ | R₁₇ | X | Y | Z | m.p. (°C.) |
|---|---|---|---|---|---|---|---|
| H | H | H | H | CH₃ | CH₃ | CH | |
| H | H | H | H | CH₃ | OCH₃ | CH | |
| H | H | H | H | OCH₃ | OCH₃ | CH | |
| H | H | H | H | CH₃ | CH₃ | N | |
| H | H | H | H | CH₃ | OCH₃ | N | |
| H | H | H | H | OCH₃ | OCH₃ | N | |
| H | H | H | H | CH₃ | CH₂OCH₃ | CH | |
| H | H | H | H | CH₃ | CH(OCH₃)₂ | CH | |
| H | H | H | H | OCH₃ | N(CH₃)₂ | N | |
| H | H | H | H | OCH₃ | NH₂ | CH | |
| H | H | H | H | Cl | OCH₃ | CH | |

TABLE VIII-continued

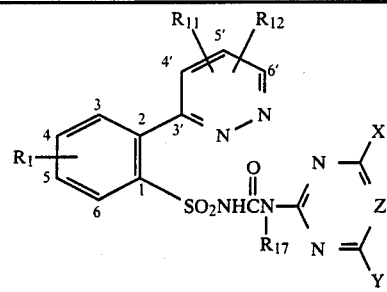

| R₁ | R₁₁ | R₁₂ | R₁₇ | X | Y | Z | m.p. (°C.) |
|---|---|---|---|---|---|---|---|
| H | H | H | H | OCH₃ | NHCH₃ | CH | |
| H | H | H | H | CH₃ | CH₂OCH₃ | N | |
| H | H | H | H | Cl | CH₃ | CH | |
| H | H | H | H | OCH₃ | CH(OCH₃)₂ | N | |
| H | 6'-CH₃ | H | H | CH₃ | OCH₃ | N | |
| H | 4'-CH₃ | 6'-CH₃ | H | OCH₃ | OCH₃ | CH | |
| H | 6'-CH₃ | H | H | OCH₃ | OCH₃ | N | |
| H | 5'-CH₃ | H | H | CH₃ | CH₃ | N | |
| H | 4'-CH₃ | 5'-CH₃ | H | OCH₃ | CH₃ | CH | |
| H | 6'-CH₃ | H | H | CH₃ | OCH₃ | CH | |
| H | H | H | CH₃ | CH₃ | CH₃ | CH | |
| H | H | H | CH₃ | OCH₃ | OCH₃ | CH | |
| H | 6'-CH₃ | H | H | CH₃ | CH₃ | N | |
| H | H | H | H | OCH₃ | CH₂OCH₃ | N | |
| H | 4'-CH₃ | H | H | CH₃ | CH₃ | CH | |
| H | H | H | H | OCH₃ | CH(OCH₃)₂ | CH | |
| 6-F | H | H | H | CH₃ | CH₃ | N | |
| 6-F | H | H | H | OCH₃ | CH₃ | N | |
| 6-F | H | H | H | CH₃ | N(CH₃)₂ | CH | |
| 6-F | H | H | H | Cl | OCH₃ | CH | |
| 6-F | H | H | CH₃ | OCH₃ | NH₂ | N | |
| 6-F | H | H | H | CH₃ | OCH₃ | N | |
| 5-Cl | H | H | H | OCH₃ | CH₃ | CH | |
| 5-Cl | H | H | H | CH₃ | OC₂H₅ | CH | |
| 5-Cl | 6'-CH₃ | H | H | OCH₃ | C₂H₅ | N | |
| 5-Cl | H | H | H | Cl | CH₂OCH₃ | N | |
| 5-Cl | H | H | H | OCH₃ | OCH₃ | CH | |
| 5-Cl | H | H | CH₃ | CH₃ | OCH₃ | CH | |
| 3-CH₃ | H | H | H | OCH₃ | NHCH₃ | N | |
| 3-CH₃ | H | H | H | CH₃ | C₂H₅ | N | |
| 3-CH₃ | H | H | H | OCH₃ | CH₃ | CH | |
| 3-CH₃ | H | H | H | CH₃ | CH₃ | CH | |
| 3-CH₃ | H | H | H | OCH₃ | CH₃ | N | |
| 4-OCH₃ | H | H | H | CH₃ | OCH₃ | N | |
| 4-OCH₃ | H | H | H | OCH₃ | OCH₃ | CH | |
| 4-OCH₃ | H | H | H | CH₃ | CH₃ | CH | |
| 4-OCH₃ | H | H | H | OCH₃ | OCH₃ | N | |

TABLE IX

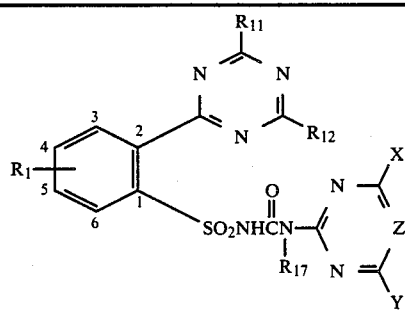

| R₁ | R₁₁ | R₁₂ | R₁₇ | X | Y | Z | m.p. (°C.) |
|---|---|---|---|---|---|---|---|
| H | CH₃ | CH₃ | H | CH₃ | CH₃ | CH | |
| H | CH₃ | CH₃ | H | CH₃ | OCH₃ | CH | |
| H | CH₃ | CH₃ | H | OCH₃ | OCH₃ | CH | |
| H | CH₃ | CH₃ | H | OCH₃ | OCH₃ | N | |
| H | CH₃ | CH₃ | H | CH₃ | OCH₃ | N | |
| H | CH₃ | CH₃ | H | OCH₃ | OCH₃ | N | |
| H | OCH₃ | OCH₃ | H | CH₃ | CH₃ | CH | |
| H | OCH₃ | OCH₃ | H | Cl | OCH₃ | CH | |
| H | OCH₃ | OCH₃ | H | OCH₃ | OCH₃ | CH | |

TABLE IX-continued

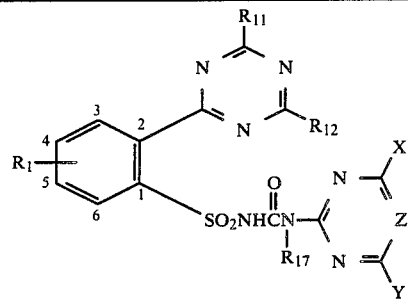

| R₁ | R₁₁ | R₁₂ | R₁₇ | X | Y | Z | m.p. (°C.) |
|---|---|---|---|---|---|---|---|
| H | OCH₃ | OCH₃ | H | CH₃ | CH₃ | N | |
| H | OCH₃ | OCH₃ | H | CH₃ | OCH₃ | N | |
| H | OCH₃ | OCH₃ | H | OCH₃ | OCH₃ | N | |
| H | OCH₃ | CH₃ | H | CH₃ | CH₃ | CH | |
| H | OCH₃ | CH₃ | H | CH₃ | OCH₃ | CH | |
| H | OCH₃ | CH₃ | H | OCH₃ | OCH₃ | CH | |
| H | OCH₃ | CH₃ | H | CH₃ | CH₃ | N | |
| H | OCH₃ | CH₃ | H | CH₃ | OCH₃ | N | |
| H | OCH₃ | CH₃ | H | OCH₃ | OCH₃ | N | |
| H | OCH₃ | CH₃ | H | CH₃ | CH₂OCH₃ | CH | |
| H | OCH₃ | CH₃ | H | CH₃ | N(CH₃)₂ | CH | |
| H | OCH₃ | CH₃ | CH₃ | OCH₃ | CH₃ | CH | |
| H | OCH₃ | CH₃ | CH₃ | CH₃ | CH(OCH₃)₂ | CH | |
| H | OCH₃ | CH₃ | CH₃ | CH₃ | CH₃ | CH | |
| 3-Cl | CH₃ | CH₃ | H | CH₃ | CH₃ | CH | |
| 3-Cl | CH₃ | CH₃ | H | CH₃ | OCH₃ | CH | |
| 3-Cl | CH₃ | CH₃ | H | OCH₃ | CH₂OCH₃ | CH | |
| 4-Cl | CH₃ | CH₃ | H | CH₃ | CH₃ | N | |
| 5-Cl | CH₃ | CH₃ | H | CH₃ | OCH₃ | N | |
| 5-Cl | CH₃ | CH₃ | H | OCH₃ | CH(OCH₃)₂ | N | |
| 5-Cl | OCH₃ | OCH₃ | H | CH₃ | OCH₃ | CH | |
| 4-CH₃ | OCH₃ | OCH₃ | H | Cl | CH₃ | CH | |
| 3-CH₃ | OCH₃ | OCH₃ | H | OCH₃ | OCH₃ | CH | |
| 6-F | OCH₃ | OCH₃ | H | CH₃ | CH₃ | N | |
| 5-OCH₃ | OCH₃ | OCH₃ | H | CH₃ | CH₃ | N | |
| H | OCH₃ | OCH₃ | H | OCH₃ | N(CH₃)₂ | N | |
| H | OCH₃ | CH₃ | H | CH₃ | NH₂ | CH | |
| H | OCH₃ | CH₃ | H | CH₃ | NHCH₃ | CH | |
| H | OCH₃ | CH₃ | H | OCH₃ | CH₂OCH₃ | CH | |
| H | OCH₃ | CH₃ | H | CH₃ | CH(OCH₃)₂ | N | |
| H | OCH₃ | CH₃ | H | CH₃ | NHCH₃ | N | |
| H | OCH₃ | CH₃ | H | OCH₃ | CH₂OCH₃ | N | |
| H | OCH₃ | CH₃ | H | CH₃ | CH(OCH₃)₂ | CH | |
| H | OCH₃ | CH₃ | H | CH₃ | N(CH₃)₂ | CH | |
| H | OCH₃ | CH₃ | CH₃ | OCH₃ | OCH₃ | CH | |
| H | OCH₃ | CH₃ | CH₃ | CH₃ | CH₃ | CH | |
| H | OCH₃ | CH₃ | CH₃ | CH₃ | OCH₃ | CH | |

TABLE X

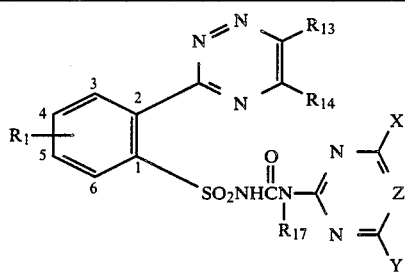

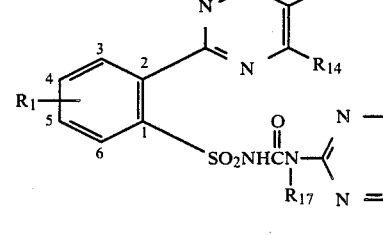

| R₁ | R₁₃ | R₁₄ | R₁₇ | X | Y | Z | m.p. (°C.) |
|---|---|---|---|---|---|---|---|
| H | CH₃ | CH₃ | H | CH₃ | CH₃ | CH | |
| H | CH₃ | CH₃ | H | CH₃ | OCH₃ | CH | |
| H | CH₃ | CH₃ | H | OCH₃ | OCH₃ | CH | |
| H | CH₃ | CH₃ | H | CH₃ | CH₃ | N | |
| H | CH₃ | CH₃ | H | CH₃ | OCH₃ | N | |
| H | CH₃ | CH₃ | H | OCH₃ | OCH₃ | N | |
| H | OCH₃ | CH₃ | H | CH₃ | CH₃ | CH | |
| H | OCH₃ | CH₃ | H | CH₃ | OCH₃ | CH | |
| H | OCH₃ | CH₃ | H | OCH₃ | OCH₃ | CH | |
| H | OCH₃ | CH₃ | H | CH₃ | CH₃ | N | |
| H | OCH₃ | CH₃ | H | CH₃ | OCH₃ | N | |
| H | OCH₃ | CH₃ | H | OCH₃ | OCH₃ | N | |
| H | OCH₃ | CH₃ | H | CH₃ | CH₂OCH₃ | CH | |
| H | OCH₃ | OCH₃ | H | CH₃ | CH₃ | CH | |
| H | OCH₃ | OCH₃ | H | CH₃ | CH₂OCH₃ | CH | |
| H | OCH₃ | OCH₃ | H | CH₃ | OCH₃ | N | |

TABLE X-continued

[Structure: benzene ring with R1 substituent at positions 3-6, position 2 bearing C(=N-N=C(R13)(R14))-N, and position 1 bearing SO2NHC(O)N group connected to a ring with X, Y, Z, R17 substituents]

| R$_1$ | R$_{13}$ | R$_{14}$ | R$_{17}$ | X | Y | Z | m.p. (°C.) |
|---|---|---|---|---|---|---|---|
| H | OCH$_3$ | OCH$_3$ | H | OCH$_3$ | OCH$_3$ | N | |
| H | OCH$_3$ | OCH$_3$ | H | Cl | OCH$_3$ | CH | |
| H | OCH$_3$ | OCH$_3$ | H | OCH$_3$ | OCH$_3$ | CH | |
| H | CH$_3$ | CH$_3$ | CH$_3$ | CH$_3$ | CH$_3$ | CH | |
| H | CH$_3$ | OCH$_3$ | CH$_3$ | CH$_3$ | OCH$_3$ | CH | |
| H | OCH$_3$ | OCH$_3$ | CH$_3$ | OCH$_3$ | CH$_3$ | N | |
| H | CH$_3$ | CH$_3$ | CH$_3$ | OCH$_3$ | OCH$_3$ | N | |
| 5-CH$_3$ | CH$_3$ | CH$_3$ | H | CH$_3$ | CH$_3$ | CH | |
| 4-Cl | CH$_3$ | CH$_3$ | H | CH$_3$ | OCH$_3$ | CH | |
| 4-Cl | CH$_3$ | CH$_3$ | H | OCH$_3$ | OCH$_3$ | CH | |
| 4-Cl | CH$_3$ | CH$_3$ | H | CH$_3$ | CH$_3$ | N | |
| 6-Cl | CH$_3$ | CH$_3$ | H | CH$_3$ | OCH$_3$ | N | |
| 3-Cl | CH$_3$ | CH$_3$ | H | OCH$_3$ | OCH$_3$ | N | |
| 5-F | OCH$_3$ | CH$_3$ | H | CH$_3$ | CH$_3$ | CH | |
| 5-F | OCH$_3$ | CH$_3$ | H | CH$_3$ | OCH$_3$ | CH | |
| 5-F | OCH$_3$ | CH$_3$ | H | OCH$_3$ | OCH$_3$ | CH | |
| 3-CH$_3$ | OCH$_3$ | CH$_3$ | H | CH$_3$ | CH$_3$ | N | |
| 3-CH$_3$ | OCH$_3$ | CH$_3$ | H | CH$_3$ | OCH$_3$ | N | |
| 3-CH$_3$ | OCH$_3$ | CH$_3$ | H | OCH$_3$ | OCH$_3$ | N | |
| 4-OCH$_3$ | OCH$_3$ | CH$_3$ | H | CH$_3$ | CH$_2$OCH$_3$ | CH | |
| 4-OCH$_3$ | OCH$_3$ | OCH$_3$ | H | CH$_3$ | CH$_3$ | CH | |
| 4-OCH$_3$ | OCH$_3$ | OCH$_3$ | H | OCH$_3$ | CH$_2$OCH$_3$ | CH | |
| 3-F | OCH$_3$ | OCH$_3$ | H | CH$_3$ | OCH$_3$ | N | |
| 3-F | OCH$_3$ | OCH$_3$ | H | OCH$_3$ | OCH$_3$ | N | |
| 3-F | OCH$_3$ | OCH$_3$ | H | Cl | OCH$_3$ | CH | |
| 4-CH$_3$ | OCH$_3$ | OCH$_3$ | H | OCH$_3$ | OCH$_3$ | CH | |
| 4-CH$_3$ | CH$_3$ | CH$_3$ | CH$_3$ | CH$_3$ | CH$_3$ | CH | |
| 4-CH$_3$ | CH$_3$ | OCH$_3$ | CH$_3$ | CH$_3$ | OCH$_3$ | CH | |
| H | OCH$_3$ | OCH$_3$ | CH$_3$ | OCH$_3$ | CH$_3$ | N | |
| H | CH$_3$ | CH$_3$ | CH$_3$ | OCH$_3$ | OCH$_3$ | N | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactan(s) and (b) about 1% to 99.9% solid or liquid inert diluent(s). More specifically, they will contain these ingredients in the following approximate proportions:

TABLE XI

| | Weight Percent* | | |
|---|---|---|---|
| | Active Ingredient | Inert Diluent(s) | Surfactant(s) |
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions. | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutecheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon surfactant granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

Further information regarding the art of formulation may be found in the following references:

G. C. Klingman, "Weed Control as a Science", John Wiley and Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 4

Wettable Powder

| | |
|---|---|
| N—[(4-methoxy-6-methylpyrimidin-2-yl)aminocarbonyl]-2-(2-pyridinyl)benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 5

Wettable Powder

| | |
|---|---|
| N—[(4,6-dimethylpyrimidin-2-yl)aminocarbonyl]-2-(2-pyridinyl)benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 6

Granule

| | |
|---|---|
| Wettable Powder of Example 5 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 7

Extruded Pellet

| | |
|---|---|
| N—[(4,6-dimethoxypyrimidin-2-yl)aminocarbonyl]-2-(2-pyridinyl)benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 8

Oil Suspension

| | |
|---|---|
| N—[(4-methoxy-6-methylpyrimidin-2-yl)aminocarbonyl]-2-(2-pyridinyl)benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 9

Wettable Powder

| | |
|---|---|
| N—[(4-methoxy-6-methylpyrimidin-2-yl)aminocarbonyl]-2-(2-pyridinyl)benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 10

Low Strength Granule

| | |
|---|---|
| N—[(4,6-dimethylpyrimidin-2-yl)aminocarbonyl]-2-(2-pyridinyl)benzenesulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 11

Aqueous Suspension

| | |
|---|---|
| N—[(4,6-dimethoxypyrimidin-2-yl)aminocarbonyl]-2-(2-pyridinyl)benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 12

Solution

| | |
|---|---|
| N—[(4-methoxy-6-methylpyrimidin-2-yl)aminocarbonyl]-2-(2-pyridinyl)benzenesulfonamide | 5% |
| water | 95% |

The salt is added directly to the water with stirring to produce the solution, which may then be packaged for use.

EXAMPLE 13

Low Strength Granule

| | |
|---|---|
| N—[(4-methoxy-6-methylpyrimidin-2-yl)aminocarbonyl]-2-(2-pyridinyl)benzenesulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 14

Granule

| | |
|---|---|
| N—[(4,6-dimethylpyrimidin-2-yl)aminocarbonyl]-2-(2-pyridinyl)benzenesulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 15

High Strength Concentrate

| | |
|---|---|
| N—[(4,6-dimethoxypyrimidin-2-yl)aminocarbonyl]-2-(2-pyridinyl)benzenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 16

Wettable Powder

| | |
|---|---|
| N—[(4-methoxy-6-methylpyrimidin-2-yl)aminocarbonyl]-2-(2-pyridinyl)benzenesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 17

Wettable Powder

| | |
|---|---|
| N—[(4-methoxy-6-methylpyrimidin-2-yl)aminocarbonyl]-2-(2-pyridinyl)benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 18

Oil Suspension

| | |
|---|---|
| N—[(4,6-dimethylpyrimidin-2-yl)aminocarbonyl]-2-(2-pyridinyl)benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 19

Dust

| | |
|---|---|
| N—[(4-methoxy-6-methylpyrimidin-2-yl)aminocarbonyl]-2-(2-pyridinyl)benzenesulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 20

Emulsifiable Concentrate

| | |
|---|---|
| N—[(4,6-dimethoxypyrimidin-2-yl)aminocarbonyl]-2-(2-pyridinyl)benzenesulfonamide | 20% |
| chlorobenzene | 74% |
| sorbitan monostearate and polyoxyethylene condensates thereof | 6% |

The ingredients are combined and stirred to produce a solution which can be emulsified in water for application.

Utility

The compounds of the present invention are highly active herbicides. They can be used for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful for plant growth modification, particularly in retarding the growth of undesired vegetation.

Rates of application for the compounds of this invention are ordinarily determined by a number of factors, including their use as either herbicides or plant growth modifiers, the types of weeds to be controlled, weather and climate, the formulation to be used, the mode of application, amount of foliage present, etc. In general terms, the subject compounds should be applied at levels of around 0.001 to 5 kg/ha, lower rates being preferred for lighter soils and/or those having a low organic matter content, for situations where only shortterm persistence is required, or for plant growth modification.

The compounds of the invention may be used in combination with any other commercial herbicide, examples of which are those of the triazine, triazole, uracil, urea, amide, diphenylether, carbamate and bipyridylium types.

The herbicidal and plant growth modifying properties of the subject compounds were discovered in a number of greenhouse tests, the results of which may be seen in the following examples.

Compounds

Compound 1
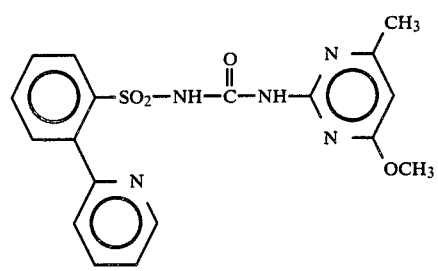

Compound 2
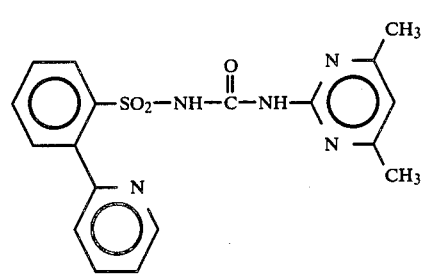

Compound 3
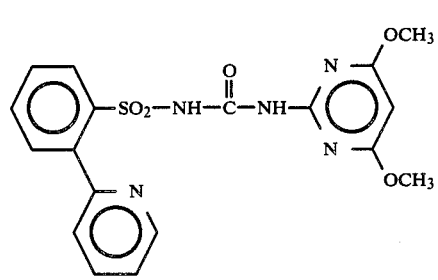

Compound 4
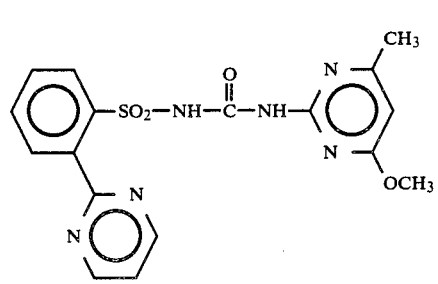

Test A

Seeds of crabgrass (Digitaria, spp.) barnyard-grass (Echinochloa crusgalli), wild oats (Avena fatua), sicklepod (Cassia obtusifolia), morningglory (Ipomoea spp.), cocklebur (Xanthium pensylvanicum), sorghum, corn, soybean, sugar beet, rice, wheat, and purple nutsedge (Cyperus rotundus) tubers were planted and treated pre-emergence with the test chemicals dissolved in a non-phytotoxic solvent. At the same time, these crop and weed species, along with cotton and bush bean, were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
E=emergence inhibition;
G=growth retardation;
H=formative effect; and
6Y=abscised buds or flowers.

TABLE A

| Rate kg/ha | Cmpd. 1 0.05 | Cmpd. 2 0.05 | Cmpd. 3 0.05 | Cmpd. 4 0.05 |
|---|---|---|---|---|
| POST-EMERGENCE | | | | |
| Bush bean | 4C,9G,6Y | 4H,6Y | 6C,9G,6Y | 9C |
| Cotton | 4C,9G | 5C,7H | 5C,9G | 4C,9G |
| Morningglory | 9C | 4C,8H | 5C,9G | 10C |
| Cocklebur | 9C | 4C,8H | 4C,9G | 10C |
| Sicklepod | 5C,7H | 2C | 3C,9G | 9C |
| Nutsedge | 2C,9G | 3C,8G | 2C,9G | 6C,9G |
| Crabgrass | 3C,8G | 2C,4H | 2C,8H | 6C,9G |
| Barnyardgrass | 3C,9H | 3C,8H | 5C,9H | 9C |
| Wild Oats | 3C,9G | 3C,8H | 2C,9G | 9C |
| Wheat | 2C,9G | 2C,3H | 2C,7G | 9C |
| Corn | 3C,9G | 4C,9H | 3C,9H | 10C |
| Soybean | 5C,9G | 3C,9G | 5C,9G | 9C |
| Rice | 5C,9G | 6C,9G | 5C,9G | 6C,9G |
| Sorghum | 3C,9H | 5C,9H | 2C,9H | 6C,9G |
| Sugar beet | 4C,8G | 2C,4G | 2C,9G | 9C |
| PRE-EMERGENCE | | | | |
| Morningglory | 9C | 2C,6H | 9C | 3C,9H |
| Cocklebur | 9H | 5H,2C | 9H | — |
| Sicklepod | 9C | 3H | 2C,9G | 2C,9G |
| Nutsedge | 3G | 0 | 10E | 10E |
| Crabgrass | 1C,2H | 4G | 2C,5G | 3C,7G |
| Barnyardgrass | 5C,9H | 2C,4G | 4C,9H | 3C,9H |
| Wild Oats | 5C,9G | 2C,5G | 2C,9G | 3C,9H |
| Wheat | 3C,9G | 2C,3G | 2C,9G | 3C,9H |
| Corn | 3C,9G | 3C,5G | 3C,9H | 10E |
| Soybean | 4C,7H | 2C | 3C,9H | 9H |
| Rice | 5C,9H | 3C,5G | 10E | 10E |
| Sorghum | 5C,9H | 3C,7H | 5C,9H | 5C,9H |
| Sugar beet | 5C,9G | 3C,5H | 9G | 10E |

Test B

Two plastic bulb pans were filled with fertilized and limed Woodstown sandy loam. One pan was planted with corn, sorghum, Kentucky bluegrass and several grass weeds. The other pan was planted with cotton, soybeans, purple nutsedge (Cyperus rotundus), and several broadleaf weeds. The following grass and broadleaf weeds were planted: crabgrass (Digitaria sanguinalis), barnyardgrass (Echinochloa crusgalli), wild oats (Avena fatua), johnsongrass (Sorghum halepense), dallisgrass (Paspalum dilatatum), giant foxtail (Setaria faberii), cheatgrass (Bromus secalinus), mustard (Brassica arvensis), cocklebur (Xanthium pensylvanicum), morningglory (Ipomoea hederacea), sicklepod (Cassia obtusifolia), teaweed (Sida spinosa), velvetleaf (Abutilon theophrasti), and jimsonweed (Datura stramonium). A 12.5 cm diameter plastic pot was also filled with prepared soil and planted with rice and wheat. Another 12.5 cm pot was planted with sugar beets. The above four containers were treated pre-emergence with one of the test compounds from within the scope of the invention.

Twenty-eight days after treatment, the plants were evaluated and visually rated for response to the chemical treatments utilizing the rating system described previously for Test A. The data are summarized in Table B.

TABLE B

PRE-EMERGENCE ON WOODSTOWN SANDY LOAM

| Rate kg/ha | Compound 1 | |
|---|---|---|
| | 0.03 | 0.125 |
| Crabgrass | 0 | 3G |
| Barnyardgrass | 7G | 9G |
| Sorghum | 9G | 10C |
| Wild Oats | 5G | 7G |
| Johnsongrass | 7G | 9G |
| Dallisgrass | 6G | 8G |
| Giant foxtail | 3G | 8G |
| Ky. bluegrass | 6G | 9G |
| Cheatgrass | 8G | 9G |
| Sugar beets | 6G | 8G |
| Corn | 6G,5H | 10C |
| Mustard | 9G | 9G |
| Cocklebur | 7G | 9G |
| Pigweed | — | — |
| Nutsedge | 5G | 6G |
| Cotton | 3G | 6G |
| Morningglory | 6G | 7G |
| Sicklepod | 3G | 7G |
| Teaweed | 4G | 7G |
| Velvetleaf | 6G | 8G |
| Jimsonweed | 6G | 9G |
| Soybean | 4G,3C | 7G,7H |
| Rice | 8G | 10C |
| Wheat | 2G | 6G |

Test C

The test chemical, dissolved in a non-phytotoxic solvent, was applied in an overall spray to the foliage and surrounding soil of selected plant species. One day after treatment, plants were checked for rapid burn injury. Approximately fourteen days after treatment all species were visually compared to untreated controls and rated for response to treatment. The rating system was as described previously for Test A. The data are presented in Table C.

All plant species were seeded in Woodstown sandy loam soil and grown in a greenhouse. The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), sicklepod (*Cassia obtusifolia*), morningglory (*Ipomoea hederacea*), jimsonweed (*Datura stramonium*), cocklebur (*Xanthium pensylvanicum*), crabgrass (Digitaria spp.), nutsedge (*Cyperus esculentus*), barnyardgrass (*Echinochloa crusgalli*), giant foxtail (*Setaria faberii*), bindweed (*Convolvulus arvensis*) and wild oats (*Avena fatua*). The following species were grown in soil in a paper cup (12 cm diameter by 13 cm deep): sunflower, sugar beets, and rape. All plants were sprayed approximately 14 days after planting.

The results of this test demonstrate the herbicidal activity of the test compound when applied as a soil/foliage treatment. It may also be seen that the treatments retard the growth of several plant species.

TABLE C

Over-the-Top Soil/Foliage Treatment

| Rate kg/ha | Compound 4 | | |
|---|---|---|---|
| | 0.25 | 0.063 | 0.016 |
| Soybeans | 9C | 10C | 10C |
| Velvetleaf | 7G | 9G | 10C |
| Sesbania | 6G | 9G | 10C |
| Sicklepod | 4C,6G | 8G | 9G |
| Cotton | 9G | 9G | 9C |
| Morningglory | 3G,4C | 6G,6C | 5C,7G |
| Alfalfa | 8G | 9C | 10C |
| Jimsonweed | 9G | 10C | 10C |
| Cocklebur | 8G | 9G | 10C |
| Corn | 3C,7G | 6G,7C | 10C |
| Crabgrass | 7G | 9G | 9G |
| Rice | 3C,4G | 6C,3G | 5G,4C |
| Nutsedge | 6C,5G | 7G | 8G |
| Barnyardgrass | 6G,6C | 7G,6C | 8G,4C |
| Wheat | 7G | 8G | 8G |
| Giant foxtail | 9G | 10C | 10C |
| Wild Oats | 6G,4C | 7G,7C | 8G,7C |
| Sorghum | 8G | 8G | 10C |
| Sunflower | 10C | 10C | 10C |
| Rape | 8G | 10C | 10C |
| Johnsongrass | 7G | 9G | 10C |
| Sugar beets | 9G | 10C | 10C |
| Bindweed | 7G | 8G | 10C |

What is claimed is:
1. A compound of the formula:

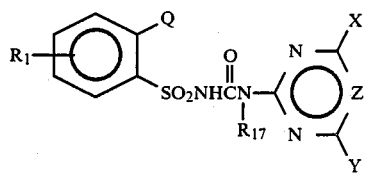

wherein
Q is

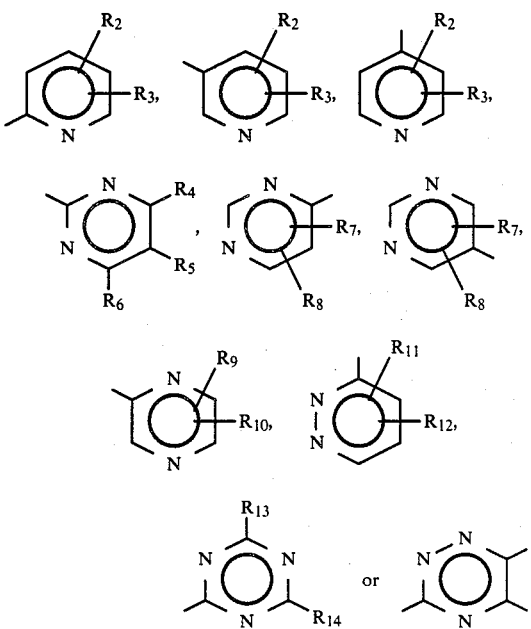

$R_1$ is H, F, Cl, $CH_3$ or $OCH_3$;
$R_2$, $R_3$, $R_5$, $R_9$, $R_{10}$, $R_{11}$, $R_{12}$ and $R_{17}$ are independently H or $CH_3$;

R7, R8, R4 and R6 are independently H, CH3 or OCH3;

R13, R14, R15 and R16 are independently CH3 or OCH3;

X is CH3 or OCH3;

Y is CH3, C2H5, CH2OCH3, OCH3, OC2H5, CH(OCH3)2 NH2, NHCH3 or N(CH3)2;

Z is N;

provided that when R1 is CH3, it is in the 3-, 4- or 5-position of the benzene ring;

and their agriculturally suitable salts.

2. Compounds of claim 1 wherein R1 and R17 are H and Y is CH3, OCH3, CH2OCH3 or N(CH3)2.

3. Compounds of claim 2 where Q is

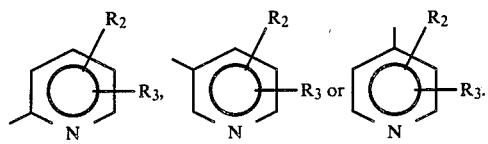

4. Compounds of claim 2 where Q is

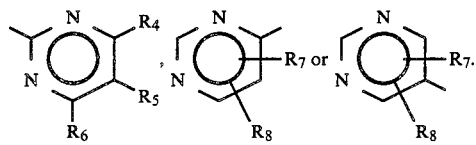

5. Compounds of claim 2 where

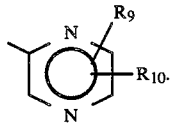

6. Compounds of claim 2 where Q is

7. Compounds of claim 2 where Q is

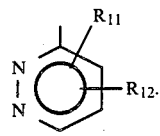

8. Compounds of claim 2 where Q is

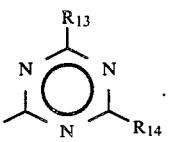

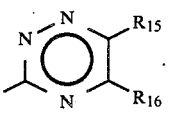

9. A composition suitable for controlling the growth of undesired vegetation which comprises an effective amount of a compound of claim 1 and at least one of the following: surfactant, solid or liquid inert diluent.

10. A composition suitable for controlling the growth of undesired vegetation which comprises an effective amount of a compound of claim 2 and at least one of the following: surfactant, solid or liquid inert diluent.

11. A composition suitable for controlling the growth of undesired vegetation which comprises an effective amount of a compound of claim 3 and at least one of the following: surfactant, solid or liquid inert diluent.

12. A method for controlling the growth of undesired vegetation which comprises applying to the locus to be protected an effective amount of a compound of claim 1.

13. A method for controlling the growth of undesired vegetation which comprises applying to the locus to be protected an effective amount of a compound of claim 2.

14. A method for controlling the growth of undesired vegetation which comprises applying to the locus to be protected an effective amount of a compound of claim 3.

* * * * *